US008666468B1

(12) United States Patent
Al-Ali

(10) Patent No.: US 8,666,468 B1
(45) Date of Patent: Mar. 4, 2014

(54) PATIENT MONITOR FOR DETERMINING MICROCIRCULATION STATE

(75) Inventor: Ammar Al-Ali, San Juan Capistrano, CA (US)

(73) Assignee: Masimo Corporation, Irvine, CA (US)

( * ) Notice: Subject to any disclaimer, the term of this patent is extended or adjusted under 35 U.S.C. 154(b) by 338 days.

(21) Appl. No.: 13/101,093

(22) Filed: May 4, 2011

Related U.S. Application Data

(60) Provisional application No. 61/332,155, filed on May 6, 2010.

(51) Int. Cl.
  *A61B 5/1455* (2006.01)
(52) U.S. Cl.
  USPC .......................... 600/324; 600/310; 600/322
(58) Field of Classification Search
  USPC .................................................. 600/310–344
  See application file for complete search history.

(56) References Cited

U.S. PATENT DOCUMENTS

| | | | |
|---|---|---|---|
| 3,980,075 A * | 9/1976 | Heule | 600/479 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |

(Continued)

*Primary Examiner* — Eric Winakur
*Assistant Examiner* — Marjan Fardanesh
(74) *Attorney, Agent, or Firm* — Knobbe Martens Olson & Bear LLP

(57) ABSTRACT

As placement of a physiological monitoring sensor is typically at a sensor site located at an extremity of the body, the state of microcirculation, such as whether vessels are blocked or open, can have a significant effect on the readings at the sensor site. It is therefore desirable to provide a patient monitor and/or physiological monitoring sensor capable of distinguishing the microcirculation state of blood vessels. In some embodiments, the patient monitor and/or sensor provide a warning and/or compensates a measurement based on the microcirculation state. In some embodiments, a microcirculation determination process implementable by the patient monitor and/or sensor is used to determine the state of microcirculation of the patient.

15 Claims, 7 Drawing Sheets

(56) References Cited

U.S. PATENT DOCUMENTS

| | | |
|---|---|---|
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |

(56) References Cited

U.S. PATENT DOCUMENTS

| | | |
|---|---|---|
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,338,447 B2 * | 3/2008 | Phillips ......................... 600/438 |
| 7,340,287 B2 | 3/2008 | Mason et al. |
| 7,341,559 B2 | 3/2008 | Schulz et al. |
| 7,341,562 B2 * | 3/2008 | Pless et al. .................... 600/504 |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |

(56) References Cited

U.S. PATENT DOCUMENTS

| | | |
|---|---|---|
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 2009/0143655 A1* | 6/2009 | Shani .......................... 600/323 |

* cited by examiner

PATIENT MONITOR FOR DETERMINING MICROCIRCULATION STATE

CROSS-REFERENCE TO RELATED APPLICATIONS

This application claims the benefit of priority under 35 U.S.C. §119(e) of U.S. Provisional Application No. 61/332,155, filed May 6, 2010, titled PATIENT MONITOR FOR DETERMINING MICROCIRCULATION STATE, the entire contents of which are hereby incorporated by reference herein.

FIELD OF THE DISCLOSURE

The present disclosure relates to medical sensors and specifically to a medical sensor and/or monitor for determining the circulation state in blood vessels.

BACKGROUND OF THE DISCLOSURE

Patient monitoring of various physiological parameters of a patient is important to a wide range of medical applications. Oximetry is one of the techniques that has developed to accomplish the monitoring of some of these physiological characteristics. It was developed to study and to measure, among other things, the oxygen status of blood. Pulse oximetry—a noninvasive, widely accepted form of oximetry—relies on a sensor attached externally to a patient to output signals indicative of various physiological parameters, such as a patient's constituents and/or analytes, including for example a percent value for arterial oxygen saturation, carbon monoxide saturation, methemoglobin saturation, fractional saturations, total hematocrit, billirubins, perfusion quality, or the like. A pulse oximetry system generally includes a patient monitor, a communications medium such as a cable, and/or a physiological sensor having light emitters and a detector, such as one or more LEDs and a photodetector. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation (SpO2) and/or pulse rate.

High fidelity pulse oximeters capable of reading through motion induced noise are disclosed in U.S. Pat. Nos. 7,096,054, 6,813,511, 6,792,300, 6,770,028, 6,658,276, 6,157,850, 6,002,952 5,769,785, and 5,758,644, which are assigned to Masimo Corporation of Irvine, Calif. ("Masimo Corp.") and are incorporated by reference herein. Advanced physiological monitoring systems can incorporate pulse oximetry in addition to advanced features for the calculation and display of other blood parameters, such as carboxyhemoglobin (HbCO), methemoglobin (HbMet), total hemoglobin (Hbt), total Hematocrit (Hct), oxygen concentrations, glucose concentrations, blood pressure, electrocardiogram data, temperature, and/or respiratory rate as a few examples. Typically, the physiological monitoring system provides a numerical readout of and/or waveform of the measured parameter. Advanced physiological monitors and multiple wavelength optical sensors capable of measuring parameters in addition to SpO2, such as HbCO, HbMet and/or Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Laboratories, Inc. and incorporated by reference herein. Further, noninvasive blood parameter monitors and optical sensors including Rainbow™ adhesive and reusable sensors and RAD-57™ and Radical-7™ monitors capable of measuring SpO2, pulse rate, perfusion index (PI), signal quality (SiQ), pulse variability index (PVI), HbCO and/or HbMet, among other parameters, are also commercially available from Masimo Corp.

During blood circulation, arteries carry blood away from the heart in high volume and under high pressure. Arteries branch off into smaller blood vessels, called arterioles. Arterioles are well innervated, surrounded by smooth muscle cells, and are about 10-100 μm in diameter. Arterioles carry the blood to the capillaries, which are the smallest blood vessels, which are not innervated, have no smooth muscle, and are about 5-8 μm in diameter. Blood flows out of the capillaries into the venules, which have little smooth muscle and are about 10-200 μm in diameter. The blood flows from venules into the veins, which carry blood back to the heart.

Microcirculation generally refers to the vascular network lying between the arterioles and the venules, including the capillaries, as well as the flow of blood through this network. These small vessels can be found in the vasculature which are embedded within organs and are responsible for the distribution of blood within tissues as opposed to larger vessels in the macrocirculation which transport blood to and from the organs. One of the functions of microcirculation is to deliver oxygen and other nutrients to tissue. Sometimes, microcirculation in these small vessels can become blocked, interfering with the delivery of oxygen to the tissue.

SUMMARY OF THE DISCLOSURE

As placement of a physiological monitoring sensor is typically at a sensor site located at an extremity of the body, the state of microcirculation, such as whether vessels are blocked or open, can have a significant effect on the readings at the sensor site. It is therefore desirable to provide a patient monitor and/or physiological monitoring sensor capable of distinguishing the microcirculation state of blood vessels. In some embodiments, the patient monitor and/or sensor provide a warning and/or compensates a measurement based on the microcirculation state. In some embodiments, a microcirculation determination process implementable by the patient monitor and/or sensor is used to determine the state of microcirculation of the patient.

BRIEF DESCRIPTION OF THE DRAWINGS

Throughout the drawings, reference numbers may be re-used to indicate correspondence between referenced elements. The drawings are provided to illustrate embodiments of the disclosure described herein and not to limit the scope thereof.

DETAILED DESCRIPTION

Figure 1:
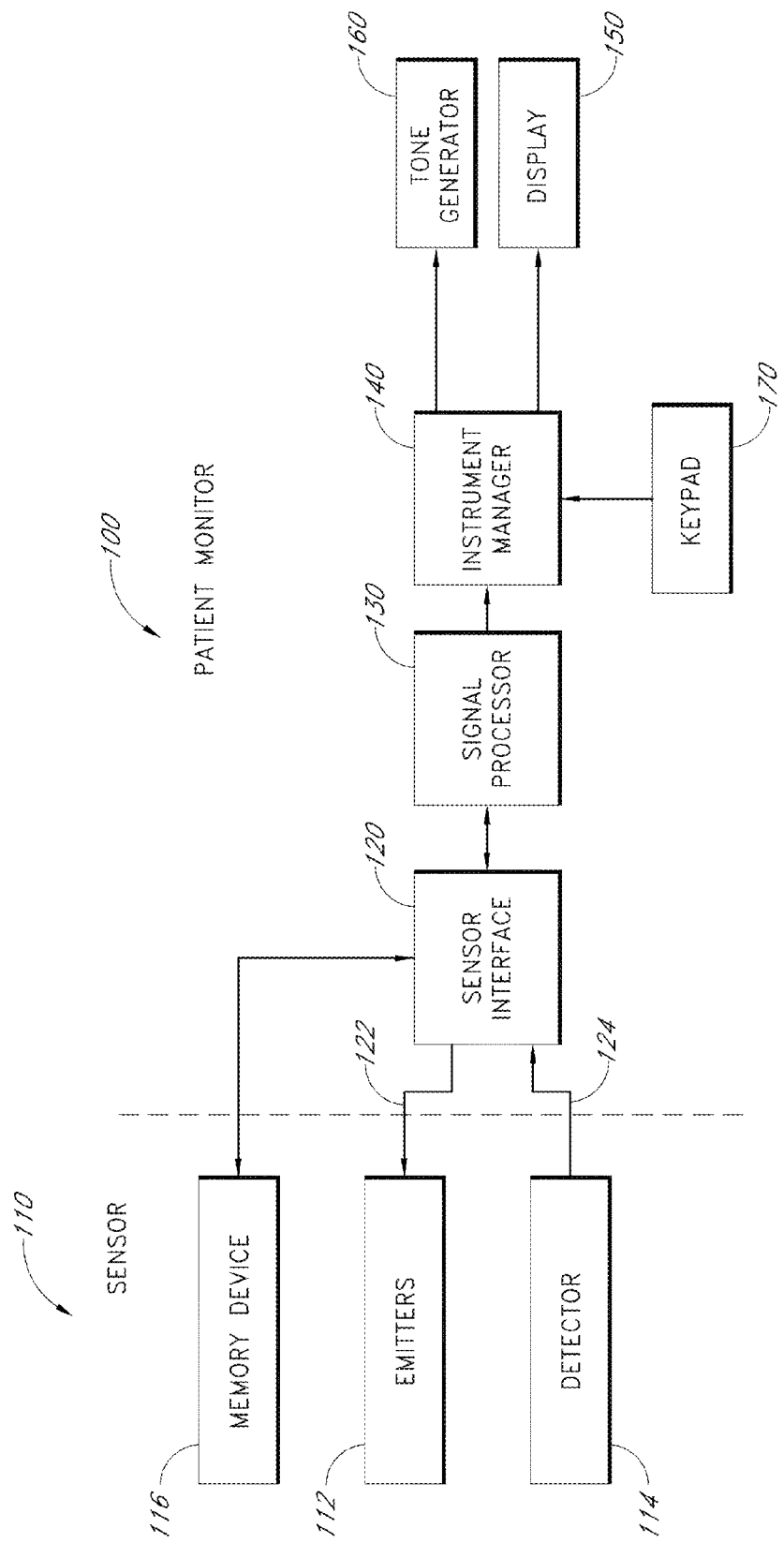
FIG. 1 illustrates a block diagram of a patient monitor, such as a pulse oximeter, and associated sensor.

FIG. 1 illustrates a block diagram of a patient monitor 100, such as a pulse oximeter, and associated sensor 110. Generally, in the case of a pulse oximeter, the sensor 110 has LED emitters 112, generally one at a red wavelength and one at an infrared wavelength, and a photodiode detector 114. The sensor 110 is generally attached to an adult patient's finger or an infant patient's foot. For a finger, the sensor 110 is configured so that the emitters 112 project light through the fingernail and through the blood vessels and capillaries underneath. The LED emitters 112 are activated by drive signals 122 from the pulse oximeter 100. The detector 114 is positioned at the fingertip opposite the fingernail so as to detect the LED emitted light as it emerges from the finger tissues. The photodiode generated signal 124 is relayed by a cable to the pulse oximeter 100.

A pulse oximeter 100 determines oxygen saturation (402) by computing the differential absorption by arterial blood of the two wavelengths emitted by the sensor 110. A typical pulse oximeter 100 contains a sensor interface 120, one or more processors 130, such as a SpO2 processor, an instrument manager 140, a display 150, an audible indicator (tone generator) 160, and a keypad 170. The sensor interface 120 provides LED drive current 122 which alternately activates the sensor's red and infrared LED emitters 112. The sensor interface 120 also has input circuitry for amplification and filtering of the signal 124 generated by the photodiode detector 114, which corresponds to the red and infrared light energy attenuated from transmission through the patient tissue site. The SpO2 processor 130 calculates a ratio of detected red and infrared intensities, and an arterial oxygen saturation value is empirically determined based on that ratio. The instrument manager 140 provides hardware and software interfaces for managing the display 150, audible indicator 160, and keypad 170. The display 150 shows the computed oxygen saturation status, as described above. Similarly, other patient parameters including HbCO, HbMet, Hbt, Hct, oxygen concentrations, glucose concentrations, pulse rate, PI, SiQ, and/or PVI can be computed. The audible indicator 160 provides the pulse beep as well as alarms indicating desaturation events. The keypad 170 provides a user interface for such things as alarm thresholds, alarm enablement, and/or display options.

Computation of SpO2 relies on the differential light absorption of oxygenated hemoglobin, $HbO_2$, and deoxygenated hemoglobin, Hb, to determine their respective concentrations in the arterial blood. Specifically, pulse oximetry measurements are made at red (R) and infrared (IR) wavelengths chosen such that deoxygenated hemoglobin absorbs more red light than oxygenated hemoglobin, and, conversely, oxygenated hemoglobin absorbs more infrared light than deoxygenated hemoglobin, for example 660 nm (R) and 905 nm (IR).

To distinguish between tissue absorption at the two wavelengths, the red and infrared emitters 112 are provided drive current 122 so that only one is emitting light at a given time. For example, the emitters 112 can be cycled on and off alternately, in sequence, with each only active for a quarter cycle and with a quarter cycle separating the active times. This allows for separation of red and infrared signals and removal of ambient light levels by downstream signal processing. Because only a single detector 114 is used, it responds to both the red and infrared emitted light and generates a time-division-multiplexed ("modulated") output signal 124. This modulated signal 124 is coupled to the input of the sensor interface 120.

In addition to the differential absorption of hemoglobin derivatives, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. This tissue site might also comprise skin, muscle, bone, venous blood, fat, pigment, and/or the like, each of which absorbs light. It is assumed that the background absorption due to these surrounding tissues is invariant and can be ignored. Thus, blood oxygen saturation measurements are based upon a ratio of the time-varying or AC portion of the detected red and infrared signals with respect to the time-invariant or DC portion: $R/IR=(Red_{AC}/Red_{DC})/(IR_A/IR_{DC})$.

The desired SpO2 measurement is then computed from this ratio. The relationship between R/IR and SpO2 can be determined by statistical regression of experimental measurements obtained from human volunteers and calibrated measurements of oxygen saturation. In a pulse oximeter device, this empirical relationship can be stored as a "calibration curve" in a read-only memory (ROM) look-up table so that SpO2 can be directly read-out of the memory in response to input R/IR measurements.

The pulse oximeter 100 can also measure perfusion index, PI, which is a numerical value that indicates the strength of the IR signal returned from a monitoring site and provides a relative assessment of the pulse strength at the monitoring site. The perfusion index can be defined as follows: $PI=(IR_{max}-IR_{min})/IR_{DC}$, where $IR_{max}$ is the maximum value, $IR_{min}$ is the minimum value, and $IR_{DC}$ is the average value of the invariant portion. As the light absorption characteristic of blood is typically "flatter" or less sensitive to oxygen saturation around the infrared wavelength, the infrared signal from a sensor is influenced primarily by the amount of the blood at the monitoring site, not by the level of oxygenation in the blood. Accordingly, the perfusion index, which is a numerical value that indicates the strength of the IR signal returned from a monitoring site, provides a relative assessment of the pulse strength at the monitoring site. PI values generally range from 0.02% (very weak pulse strength) to 20% (very strong pulse strength). In some embodiments, PI can be measured using other wavelengths. For example, red, near red, near IR, as well as other wavelengths can be used.

In an embodiment, the sensor 110 also includes a memory device 116. The memory 116 can include any one or more of a wide variety of memory devices known to an artisan from the disclosure herein, including erasable programmable read only memory (EPROM), electrically erasable programmable read-only memory (EEPROM), flash memory, other non-volatile memory, a combination of the same or the like. The memory 116 can include read-only memory such as read-only memory (ROM), a read and write device such as a random-access memory (RAM), combinations of the same, or the like. The remainder of the present disclosure will refer to such combination as simply EPROM for ease of disclosure; however, an artisan will recognize from the disclosure herein that the memory can include ROM, RAM, single wire memory, other types of memory, combinations of the same, or the like.

The memory device 116 can advantageously store some or all of a wide variety of data and information, including, for example, information on the type or operation of the sensor, type of patient or body tissue, buyer or manufacturer information, sensor characteristics including the number of wavelengths capable of being emitted, emitter specifications, emitter drive requirements, demodulation data, calculation mode data, calibration data, software such as scripts, executable code, or the like, sensor electronic elements, sensor life data indicating whether some or all sensor components have expired and should be replaced, encryption information, monitor or algorithm upgrade instructions or data, or the like. In an embodiment, the memory device can also include oxygen saturation to perfusion index and R/IR ratio to perfusion index ratios and/or data.

In certain situations, pulse oximetry sensors may produce anomalous readings, such as when a patient suffers from cyanosis. In a patient suffering from cyanosis, blood cells are uncharacteristically low on oxygen, leading to oxygen deficiency and giving the patient's skin a bluish-hue. One potential cause is that the patient's body produces too much hemoglobin, making the blood "thicker" or slower flowing, making microcirculation vessels more prone to blockage. Thus, a "blocked" microcirculation state can indicate cyanosis.

A "blocked" microcirculation state can also indicate other medical conditions, such as sepsis, systemic inflammatory response syndrome (SIRS), or septicemia. Sepsis is a potentially deadly medical condition that is characterized by a whole-body inflammatory state (called SIRS) and the presence of a known or suspected infection. The body may develop this inflammatory response by the immune system to microbes in the blood, urine, lungs, skin, or other tissue. Septicemia is a related medical term referring to the presence of pathogenic organisms in the bloodstream, which can lead to sepsis. Sepsis can also be referred to as blood poisoning. During sepsis or SIRS, inflammation in the body can cause constriction in blood vessels, leading to low blood pressure or insufficient blood flow.

During a "blocked" microcirculation state, blood cells can get blocked in the microcirculation vessels, such as the arterioles and capillaries. Blood cells can clump together or otherwise catch against the wall of blood vessels, creating a blockage that prevents blood cells, including red blood cells carrying hemoglobin, from passing through the blockage. However, plasma, which is composed of mostly water and in which the blood cells are suspended, is generally able to flow through passages in the blockage. In some situations, some blood vessels at the monitoring site may continue to have normal flow while some vessels are blocked. Thus, a "blocked" microcirculation state can indicate that some microcirculation vessels in an area are blocked and not necessarily all vessels in the area are blocked.

With the blockage preventing most or all the red blood cells from passing a blood vessel, at most only a limited amount of hemoglobin passes through a blocked blood vessel. In some situations, the blood vessel may only be partially blocked, where some hemoglobin passes through but less than when the blood vessel is unblocked. Normally, blood is made up of about 40-50% of red blood cells, of which about 95% is hemoglobin. Plasma, which is about 95% water, normally constitutes about 55% of the blood's volume.

Accordingly, a pulse oximeter placed on a tissue site experiencing blockage in microcirculation vessels may detect mostly plasma passing through with no or only a small percentage of red blood cells, at least at part of the monitoring site. The resulting change in the normal composition of blood can cause anomalous readings in the pulse oximetry monitor.

As plasma has generally different absorption characteristics for red and infrared wavelengths than normal blood, pulse oximetry readings may become skewed. $Red_{AC}$ and/or $IR_{AC}$ can be affected, causing measured R/IR ratio to change. For example, if $Red_{AC}$ rises or $IR_{AC}$ drops, the R/IR ratio increases. Alternatively, if $Red_{AC}$ drops or $IR_{AC}$ rises, the R/IR ratio decreases. Thus, the value of R/IR can change due to a change in the light absorption of blood even if the underlying oxygen saturation of the blood remains the same.

However, by comparing oxygen saturation and PI for normal microcirculation to the oxygen saturation and PI for blocked microcirculation, such as by calculating and comparing ratios, the monitor can determine the existence of an abnormal situation. Typically, SpO2 is mostly independent of PI, with SpO2 varying minimally as PI increases. However, SpO2 varying by more than normal as PI increases can indicate an anomalous microcirculation state, such as a blockage. In one embodiment, by analyzing the measured ratios, the pulse oximeter 100 can determine the microcirculation state, such as whether a blocked vessel exists in the microcirculation vessels.

Figure 2:
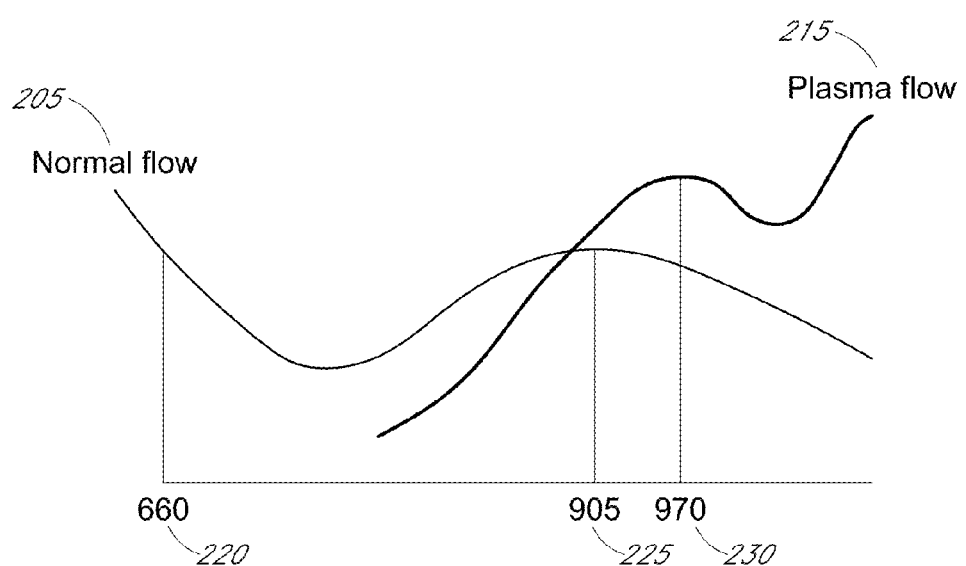
FIG. 2 illustrates an example graph depicting the optical absorption characteristic of normal blood and plasma.

FIG. 2 illustrates an example graph depicting the optical absorption characteristic of normal blood and plasma. The graph depicts sampling wavelengths at 660 nm 220 and at 905 nm 225. As illustrated, IR absorption for plasma at a frequency of 905 nm is on a "steeper" section of the curve compared to the "flatter" section of the curve for normal blood. This can imply that readings for IR for plasma would be more sensitive to changes in the absorption quality of the blood. In contrast, the IR measurement for normal blood, for example at 905 nm, is usually insensitive to a change in oxygenation of normal blood, but more affected by change in the amount of blood. As illustrated in the graph, plasma can have a "flatter" section in its absorption curve at a different wavelength, for example at 970 nm 230.

Figure 3A:
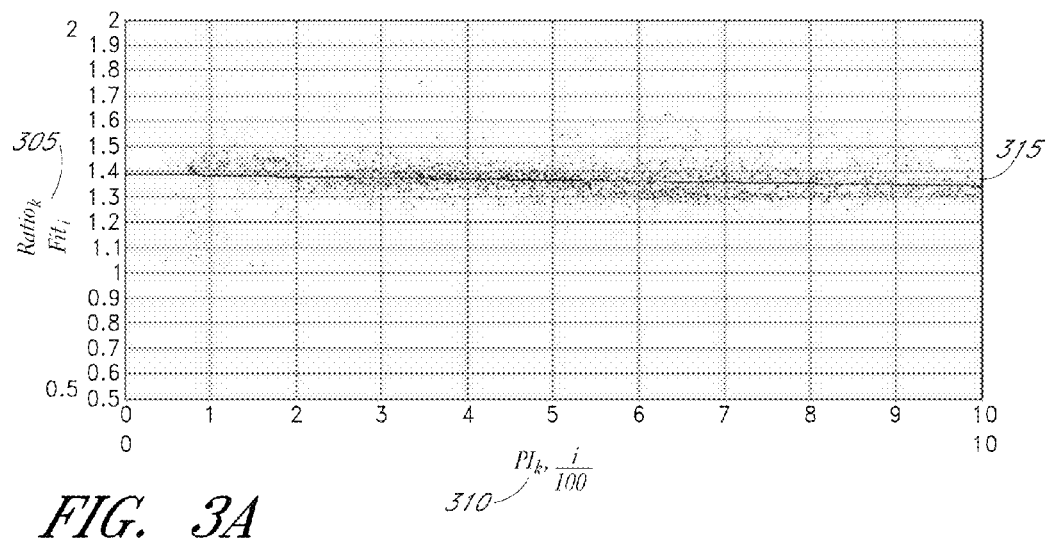
FIGS. 3A and 3B illustrate graphs of oxygen saturation values for a normal microcirculation state data set.
Figure 3B:
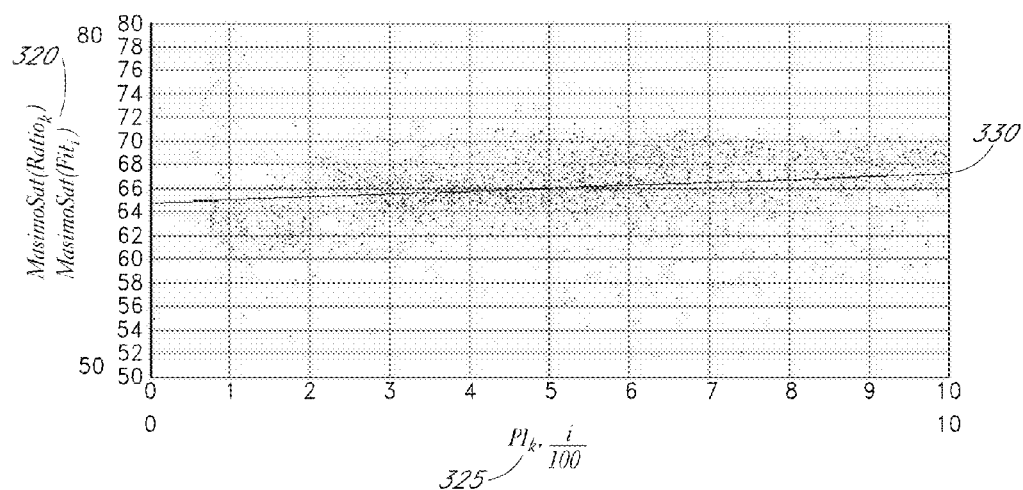

FIGS. 3A and 3B illustrate graphs of oxygen saturation values for a normal microcirculation state data set. FIG. 3A has an y-axis 305 corresponding to the measured ratio, R/IR, and a x-axis 310 corresponding to perfusion index, PI. FIG. 3B has a y-axis 320 corresponding to measured oxygen saturation, and an x-axis 325 corresponding to perfusion index, PI. FIGS. 3A and 3B represent multiple data points with a best fit line 315, 330 indicating the trend of the data points. Each data point represents a measurement. As illustrated, the best fit line for FIG. 3A trends slightly downward and the best fit line for FIG. 3B trends slightly upwards. However, there is generally only a small change in the y-axis for the best fit line as PI increases, with the change in FIG. 3A around 0.1 and the change in FIG. 3B around 4.

Figure 4A:
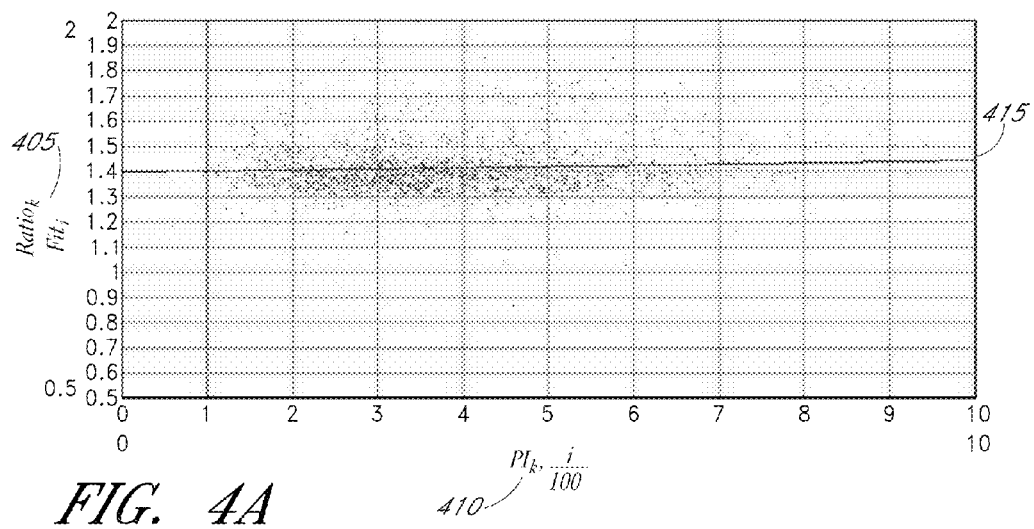
FIGS. 4A and 4B illustrate graphs of oxygen saturation values for another normal microcirculation state data set.
Figure 4B:
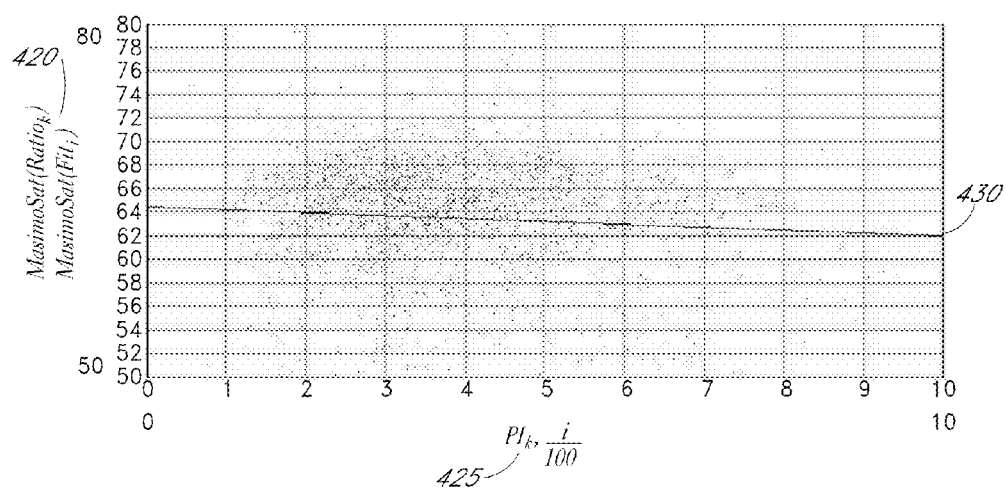

FIGS. 4A and 4B illustrate graphs of oxygen saturation values for another normal microcirculation state data set. FIG. 4A has a y-axis 405 corresponding to the measured ratio, R/IR, and an x-axis 410 corresponding to perfusion index, PI. FIG. 4B has a y-axis 420 corresponding to measured oxygen saturation, and an x-axis 425 corresponding to perfusion index, PI. FIGS. 4A and 4B represent multiple data points with a best fit line 415, 430 indicating the trend of the data points. Each data point represents a measurement. As illustrated, the best fit line for FIG. 4A trends slightly upwards and the best fit line for FIG. 4B trends slightly downwards. However, there is generally only a small change in the y-axis for the best fit line as PI increases, with the change in FIG. 4A around 0.1 and the change in FIG. 4B around 3.

Figure 5A:
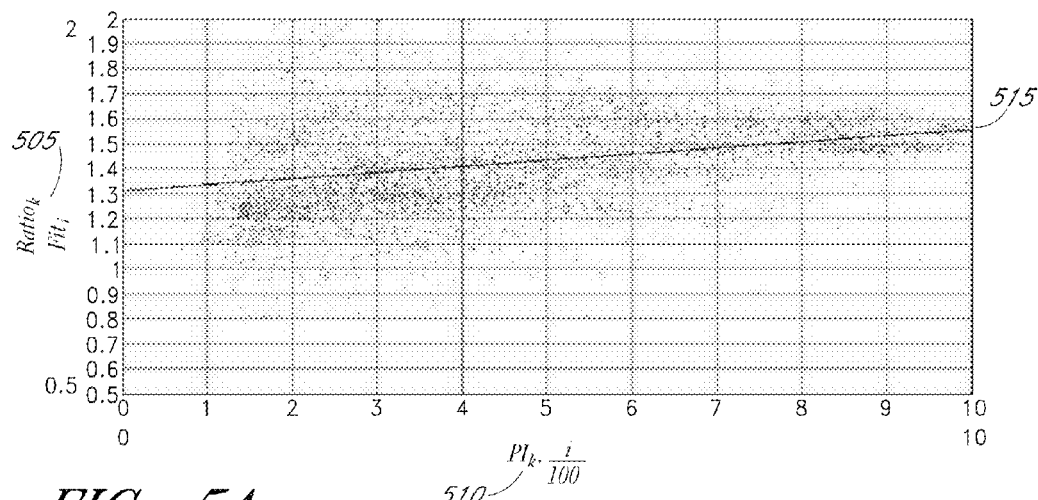
FIGS. 5A and 5B illustrate graphs of oxygen saturation values for an anomalous microcirculation state data set.
Figure 5B:
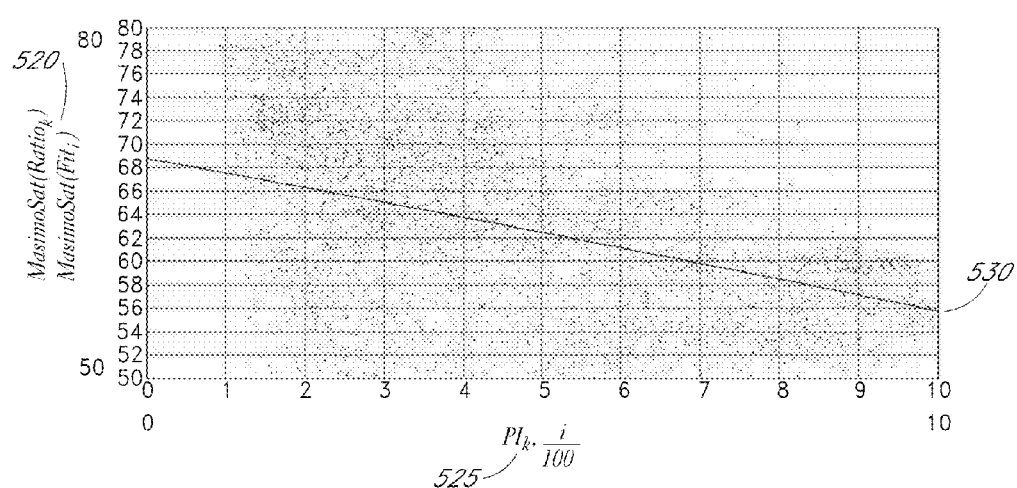

FIGS. 5A and 5B illustrate graphs of oxygen saturation values for an anomalous microcirculation state data set. FIG. 5A has a y-axis 505 corresponding to the measured ratio, R/IR, and an x-axis 510 corresponding to perfusion index, PI.

FIG. 5B has a y-axis 520 corresponding to measured oxygen saturation, and an x-axis 525 corresponding to perfusion index, PI. FIGS. 5A and 5B represent multiple data points with a best fit line 515, 530 indicating the trend of the data points. Each data point represents a measurement. As illustrated, the best fit line for FIG. 5A trends significantly upwards on the y-axis by around 0.3 and the best fit line for FIG. 5B trends significantly downwards on the y-axis by around 13 as PI increases.

In comparison to FIGS. 3A and 4A, FIG. 5A shows a high R/IR ratio for low values of PI that becomes a high R/IR ratio as PI increases. In comparison to FIGS. 3B and 4B, FIG. 5B shows a high reading for low values of PI that becomes a low reading as PI increases. Differences between the graphs can be explained by the microcirculation state in FIGS. 5A and 5B being different from the microcirculation state in FIGS. 3A-4B. For example, FIGS. 5A and 5B can represent a "blocked" or partially blocked microcirculation state where the blood passing through the sensor includes mostly plasma. As discussed above, this can skew R/IR and the measured oxygen saturation derived from R/IR.

Figure 6:
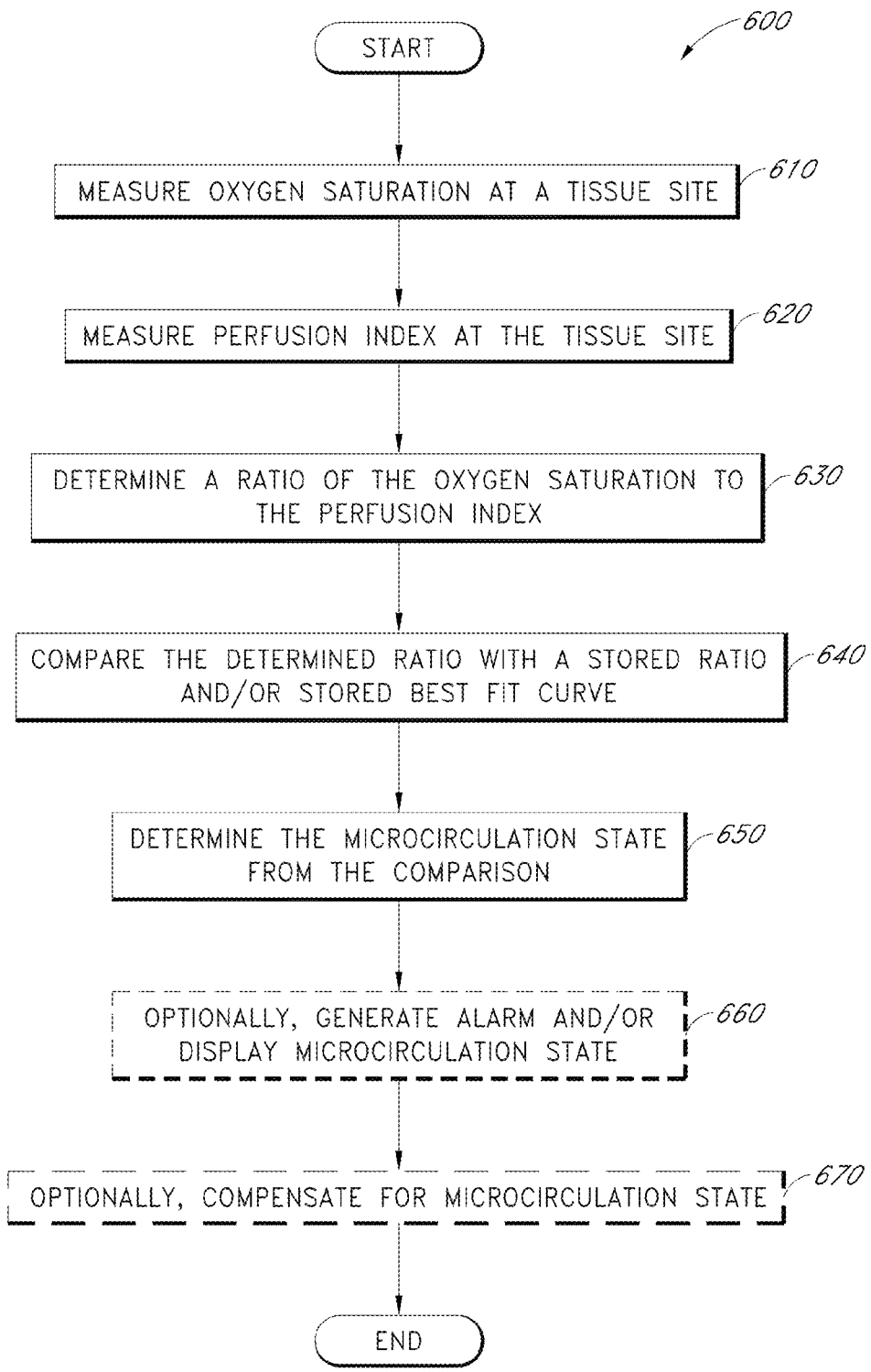
FIG. 6 illustrates a flow diagram for a process for determining the state of microcirculation usable by a pulse oximeter.

FIG. 6 illustrates a flow diagram for a process 600 for determining the state of microcirculation usable by a pulse oximeter. Microcirculation state can be determined by comparison with microcirculation data stored on a patient monitor, such as the pulse oximeter 100 of FIG. 1. The process 600 can be implemented by embodiments of the sensor 110 and/or patient monitor 100 of FIG. 1 or other suitable device.

While in conventional pulse oximetry, measurements are generally taken pulse-by-pulse and averaged over pulses, microcirculation measurements can be measured using only a single pulse or a portion of a single pulse. This can be done, for example, at the minimum and/or maximum blood flow of a pulse. Microcirculation measurements can also be determined over multiple pulses. In some embodiments, microcirculation measurements are taken during a portion of the normal measurement time used by a physiological sensor to take a measurement of a parameter, thereby allowing detection of aberrant parameter measurements using the microcirculation measurements. For example, while a pulse oxymeter is measuring SpO2 over several pulses, microcirculation measurements can be taken per pulse and a warning given if an irregular microcirculation state is detected, thereby notifying a user of a possible aberration in the current SpO2 reading.

At block 610, oxygen saturation is measured at a tissue monitoring site. In one embodiment, oxygen saturation is determined using a pulse oximeter sensor.

At block 620, perfusion index or pulse strength is measured. In one embodiment, the perfusion index is determined using the same sensor used to measure oxygen saturation so that readings are taken at the same monitoring site.

At block 630, a ratio of oxygen saturation to perfusion index is determined. Oxygen saturation can be a SpO2 value based on the measured R/IR ratio looked-up against a calibration curve. Alternatively, the ratio can be perfusion index to oxygen saturation. In other embodiments, the measured R/IR ratio can be used directly instead of SpO2.

In some embodiments, multiple readings of perfusion index and oxygen saturation can be taken and averaged together before determining the ratio in order to account for outliers. The multiple readings can be filtered before averaging. For example, readings can first be filtered based on closeness of PI values before the readings are averaged together.

At block 640, the determined ratio in block 630 is compared to stored microcirculation data. The stored data can be data sets for microcirculation states. In some embodiments, a ratio, a curve, a line, table, data points, or formula can be stored that corresponds to a data set. The measured perfusion index and oxygen saturation can then be compared to the stored data. In some embodiments, multiple readings are taken and a best fit line or curve is generated and compared to a stored best fit line or curve. In some embodiments, readings are collected at various PI values in order to generate a trend line.

At block 650, the microcirculation state is determined from comparison of the stored microcirculation data. For example, if the determined ratio is similar to a stored ratio corresponding to a data set for unblocked microcirculation, the microcirculation state is determined to be unblocked. Other data sets for other microcirculation states, such as blocked and/or partially blocked can also be stored. Where multiple data sets are stored, the state can be determined by selecting the state corresponding to the stored ratio closest to the measured ratio.

At block 660, the monitor can optionally generate an alarm and/or display the microcirculation state. For example, an alarm signal can be generated by the monitor to indicate that the readings may be anomalous, such as when a blocked or partially blocked microcirculation state is detected. The alarm can be a visual indicator (e.g., icon, message or image) and/or an audio indicator. In an embodiment, the alarm can indicate the detection of cyanosis, sepsis, SIRS or other medical condition based at least partly on the determined microcirculation state. In some situations, no action is taken, such as when readings are determined to be normal or non-threatening.

At block 670, the monitor can optionally compensate for the microcirculation state in order to improve accuracy of the readings. After the microcirculation state returns to normal, the compensation process can be ended.

In one embodiment, an offset can be added to the measured parameter value, such as 402. The offset can be calculated based on data sets for microcirculation state. Different microcirculation states can have different offsets. For example, if a "blocked" microcirculation state produces high readings for low PI values, a negative offset can be used. However, if a "blocked" state produces a low value for high PI values, then a positive offset can be used. In one embodiment, a varying offset can be used depending on the value of PI.

In one embodiment, a different wavelength emitter can be used to compensate for a microcirculation state. For example, rather than using a regular infrared emitter, typically 905 nm, an emitter with a different infrared wavelength, such as 970 nm can be used. In one embodiment, the different wavelength is selected such that the wavelength is at a "flat" section of the light absorption curve for plasma, that is, where the light absorption is not much affected by changes in oxygen saturation. In one embodiment, the selected wavelength with regards to plasma mimics the properties of the regular wavelength with regards to normal flowing blood. In some embodiments, a different wavelength red emitter can be used instead of the regular red wavelength emitter.

In some embodiments, the pulse oximeter sensor used to measure oxygen saturation and PI can be provided with an additional emitter at a different wavelength than the existing emitters. When a certain microcirculation state is detected, such as a "blocked" state, the additional emitter can be used. For example, a pulse oximetry sensor can be equipped with LED's capable of emitting at 660 nm, 905 nm, and at 970 nm wavelengths. Under normal operation, the 660 nm and 905 nm emitters are active. However, upon detecting a blocked microcirculation state, the 905 nm emitter can be deactivated and the 970 nm emitter activated in its place. In some embodiments, a variable wavelength emitter can be used rather than separate emitters. In some embodiments, the additional emitter can be a red wavelength emitter.

Figure 7:
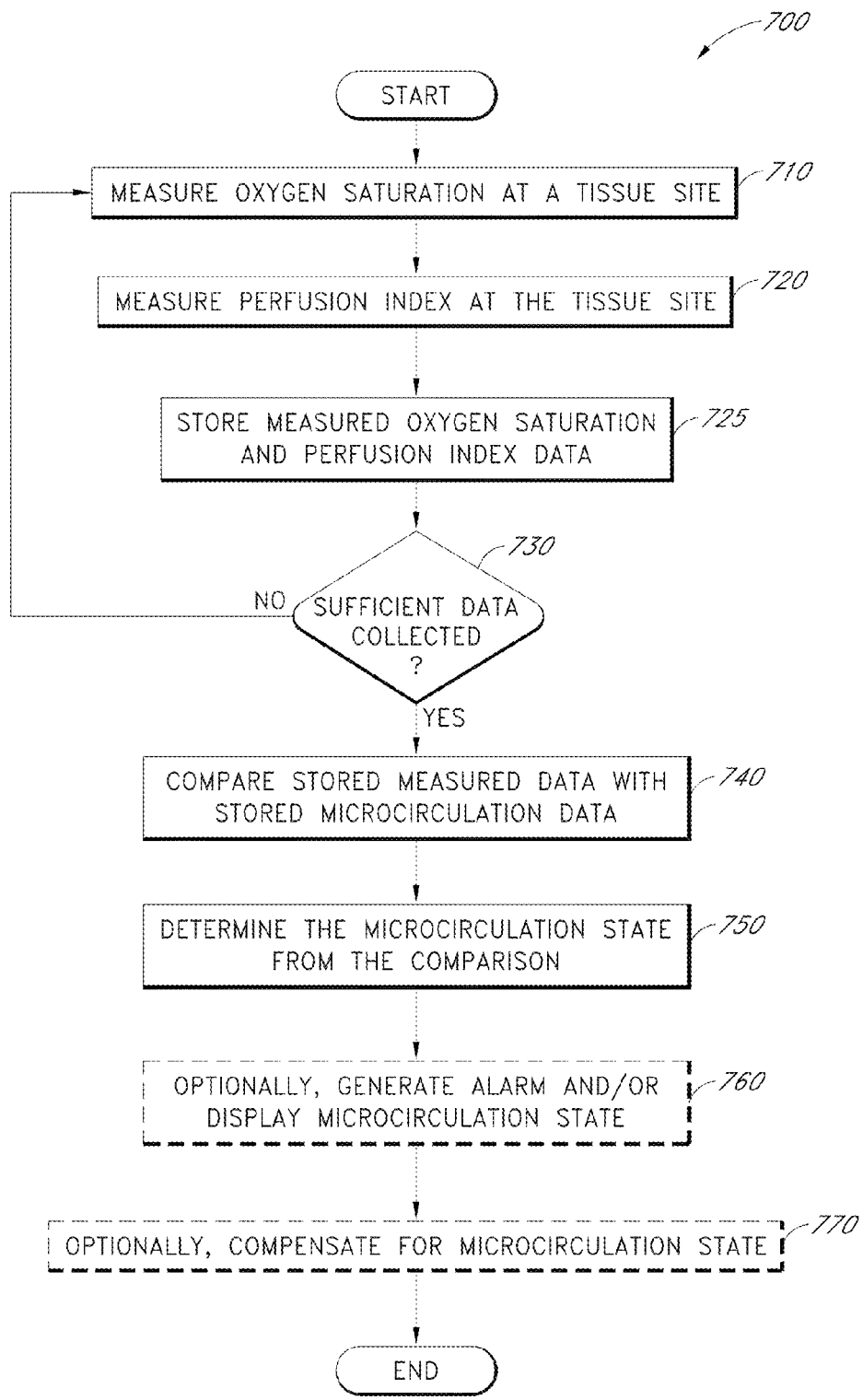
FIG. 7 illustrates a flow diagram for a process for determining the state of microcirculation wherein multiple data points are collected.

FIG. 7 illustrates a flow diagram for a process 700 for determining the state of microcirculation wherein multiple data points are collected. The process 700 can be implemented by embodiments of the sensor 110 and/or patient monitor 100 of FIG. 1 or other suitable device.

At block 710 and block 720, oxygen saturation and perfusion index are measured. At block 725, measured values are stored in memory. Each paired measurement forms a data point.

At block 730, the number of stored data points is checked to determine if sufficient data has been collected to determine the microcirculation state. Data can be sufficient if a set number of data points have been collected, a set amount of time has passed, and/or a spectrum of data points have been collected, such as for differing values of PI.

At block 740, the stored measured data is compared with stored microcirculation data. Typically, the microcirculation data is pre-stored on the pulse oximeter before use, as opposed to collected during use. A comparison can involve generating a curve or line from the measured data, calculating a rate of change for the stored data, generating a trend line for the measured data or the like and comparing with the stored microcirculation data.

At block 750, the microcirculation state is determined from comparison of the stored microcirculation data. For example, if the measured data is similar to microcirculation data corresponding to a data set for unblocked microcirculation, the microcirculation state is determined to be unblocked. Other data sets for other microcirculation states, such as for blocked and/or partially blocked can also be stored. Where multiple data sets are stored, the state can be determined by selecting the state corresponding to the stored ratio closest to the measured ratio.

Blocks 760 and 770 are similar to steps 660 and 670 described in FIG. 6.

As will be apparent from the above description, the R/IR ratio corresponds to oxygen saturation or SpO2 and can be used in place of oxygen saturation or SpO2 for the above comparisons, and vice versa.

While the above systems and methods have been described in terms of oxygen saturation and PI, other physiological parameters can be measured in place of or in addition to oxygen saturation and/or perfusion index and used to determine microcirculation state. For example, perfusion index is an indication of amplitude and/or signal strength and other parameters or measurements indicating amplitude and/or signal strength can be used. In some embodiments, one or more different sensors can be used in place of or in addition to a pulse oximeter sensor.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Various systems and processes for determining microcirculation state have been disclosed in detail in connection with various embodiments. These embodiments are disclosed by way of examples only and are not to limit the scope of the claims that follow. Indeed, the novel methods and systems described herein can be embodied in a variety of other forms; furthermore, various omissions, substitutions and changes in the form of the methods and systems described herein can be made without departing from the spirit of the inventions disclosed herein. The claims and their equivalents are intended to cover such forms or modifications as would fall within the scope and spirit of certain of the inventions disclosed herein. One of ordinary skill in the art will appreciate the many variations, modifications and combinations. For example, the various embodiments of the microcirculation determination process can be used with other oxygen saturation sensors and with both disposable and reusable sensors. In some embodiments, the determination process can be applied to other blood vessels to detect a blockage, even in vessels not involved in microcirculation.

Furthermore, in certain embodiments, the systems and methods described herein can advantageously be implemented using computer software, hardware, firmware, or any combination of software, hardware, and firmware. In one embodiment, the system includes a number of software modules that comprise computer executable code for performing the functions described herein. In certain embodiments, the computer-executable code is executed on one or more general purpose computers or processors. However, a skilled artisan will appreciate, in light of this disclosure, that any module that can be implemented using software can also be implemented using a different combination of hardware, software or firmware. For example, such a module can be implemented completely in hardware using a combination of integrated circuits. Alternatively or additionally, such a module can be implemented completely or partially using specialized computers or processors designed to perform the particular functions described herein rather than by general purpose computers or processors.

Moreover, certain embodiments of the invention are described with reference to methods, apparatus (systems) and computer program products that can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the acts specified herein to transform data from a first state to a second state.

Each of the processes, methods, and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:

1. A method of determining blood vessel flow state comprising: generating a plurality of stored data points wherein a data point comprises an oxygen saturation value and a perfusion index value, the plurality of data points generated periodically by:
   determining an oxygen saturation value of blood from measured red and infrared light absorption characteristics of tissue at a tissue monitoring site monitored by a physiological sensor;
   determining a perfusion index value from the measured infrared light absorption characteristic of the tissue at the measuring site; and
   storing the measured oxygen saturation and perfusion index;
   determining a relationship between the stored data points;
   comparing the determined relationship with stored microcirculation data corresponding to a blocked or partially blocked microcirculation state, the stored microcirculation data representing a relationship between oxygen saturation and perfusion index; and
   determining a current microcirculation state of at least a portion of blood vessels at the monitoring site from the comparison with the microcirculation data.

2. The method of claim 1, wherein determining a relationship between the stored data points comprises determining a trend from the stored data points.

3. The method of claim 1, wherein determining a relationship between the stored data points comprises:
   averaging the oxygen saturation value of at least some data points;
   averaging the perfusion index value of at least some data points; and
   generating a ratio from the average oxygen saturation value and the average perfusion index value.

4. The method of claim 1, further comprising generating an alarm signal when a blocked or partially blocked microcirculation state is detected.

5. The method of claim 1, further comprising applying an offset to a current measurement of oxygen saturation to compensate for a blocked or partially blocked microcirculation state.

6. A method of non-invasively determining blood vessel flow state comprising:
   determining one or more measurement values for a first physiological parameter at a tissue monitoring site monitored by a non-invasive physiological sensor;
   determining one or more measurement values for a second physiological characteristic monitored at the tissue monitoring site;
   determining a relationship between the first physiological parameter and the second physiological parameter;
   comparing the determined relationship with stored microcirculation data, the stored blocked or partially blocked microcirculation data corresponding to a microcirculation state of microcirculation blood vessels, the stored microcirculation data representing a relationship between the first physiological parameter and the second physiological parameter; and
   determining a current microcirculation state of at least a portion of blood vessels at the tissue monitoring site from the comparison with the microcirculation data.

7. The method of claim 6, wherein the first physiological parameter comprises oxygen saturation.

8. The method of claim 6, wherein the second physiological parameter comprises perfusion index.

9. The method of claim 6, wherein the first and second physiological parameters are monitored by the same non-invasive physiological sensor.

10. The method of claim 6, wherein determining a relationship between the first and second physiological parameters comprises generating a ratio based on the one or more measurement values of the first physiological parameters to the one or more measurement values of the second physiological parameters.

11. The method of claim 6, wherein determining a relationship between the first and second physiological parameters corresponds to generating a trend line based on the stored data points of the first and second physiological parameters.

12. The method of claim 6, wherein the stored microcirculation data comprises at least one microcirculation curve.

13. The method of claim 6, wherein the non-invasive physiological sensor comprises a pulse oximeter sensor.

14. The method of claim 6, further comprising generating an alarm signal when a blocked microcirculation state is detected.

15. The method of claim 6, further comprising applying an offset to a current measurement of oxygen saturation to compensate for a blocked microcirculation state.

* * * * *

UNITED STATES PATENT AND TRADEMARK OFFICE
CERTIFICATE OF CORRECTION

PATENT NO. : 8,666,468 B1
APPLICATION NO. : 13/101093
DATED : March 4, 2014
INVENTOR(S) : Al-Ali It is certified that error appears in the above-identified patent and that said Letters Patent is hereby corrected as shown below:

In the Specification

In column 1 at line 34, Change "billirubins," to --bilirubins,--.

In column 3 at line 25, Change "(402)" to --(SpO2)--.

In column 4 at lines 21-22, Change "R/IR=(Red$_{AC}$/Red$_{DC}$)/(IR$_A$/IR$_{DC}$)." to --R/IR=(Red$_{AC}$/Red$_{DC}$)/(IR$_{AC}$/IR$_{DC}$).--.

In column 7 at line 40, Change "oxymeter" to --oximeter--.

In column 8 at line 35, Change "402." to --SpO2.--.

In the Claims

In column 12 at lines 26-27 (approx.), In Claim 6, change "stored blocked or partially blocked microcirculation data corresponding to a microcirculation state" to --stored microcirculation data corresponding to a blocked or partially blocked microcirculation state--.

Signed and Sealed this
Twelfth Day of August, 2014

Michelle K. Lee
*Deputy Director of the United States Patent and Trademark Office*